United States Patent [19]

Oeckl et al.

[11] 4,079,148
[45] Mar. 14, 1978

[54] ANTIMICROBIAL SULFONYL-ACRYLONITRILES AND AMIDES THEREOF

[75] Inventors: Siegfried Oeckl; Wilfried Paulus; Hermann Genth, all of Krefeld, Germany

[73] Assignee: Bayer Aktiengesellschaft, Leverkusen, Germany

[21] Appl. No.: 643,578

[22] Filed: Dec. 22, 1975

[30] Foreign Application Priority Data

Jan. 4, 1975 Germany .............................. 2500265

[51] Int. Cl.² ................. A61K 31/165; A61K 31/275; C07C 103/22; C07C 121/70
[52] U.S. Cl. ................................. 424/304; 260/397.6; 260/465 G; 260/465.7; 260/558 S; 260/559 T; 260/561 S; 424/320; 424/324
[58] Field of Search ............ 260/465 G, 465.7, 558 S, 260/561 S; 424/304, 320, 324

[56] References Cited

U.S. PATENT DOCUMENTS

| 3,078,298 | 2/1963 | Gregory et al. | 260/465.4 |
| 3,140,307 | 7/1964 | Heininger et al. | 260/465 |
| 3,142,616 | 7/1964 | Baker et al. | 260/465.7 X |
| 3,437,685 | 4/1969 | Brust | 260/558 X |
| 3,541,119 | 11/1970 | Richter et al. | 260/397.6 |

*Primary Examiner*—Dolph H. Torrence
*Attorney, Agent, or Firm*—Burgess, Dinklage & Sprung

[57] ABSTRACT

Compounds useful as antimicrobial and microbicidal compounds have the formula

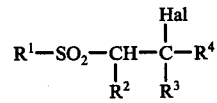

wherein
R¹ is optionally halogen-substituted lower alkyl or optionally substituted aryl,
R² is hydrogen and
R³ is halogen, or
R² and R³ conjointly represent a bond,
R⁴ is nitrile (—CN) or carboxylic acid amide (—CONH₂) and
Hal is halogen.

6 Claims, No Drawings

ANTIMICROBIAL SULFONYL-ACRYLONITRILES AND AMIDES THEREOF

This invention relates to new compounds having a microbicidal action, processes for their preparation, and their use.

SUMMARY

The new compounds correspond to the formula

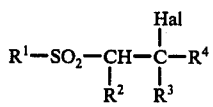

in which
$R^1$ represents an optionally halogen-substituted lower alkyl radical or an optionally substituted aryl radical,
$R^2$ represents hydrogen and
$R^3$ represents halogen or
$R^2$ and $R^3$ conjointly represent a bond,
$R^4$ represents a nitrile(—CH) or carboxylic acid amide(—CONH$_2$) group and
Hal represents halogen.

A group of the new compounds thus corresponds to the formula

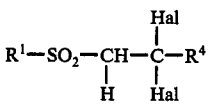

in which
$R^1$, $R^4$ and Hal have the abovementioned meaning, whilst a second group of the new compounds corresponds to the formula

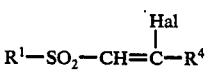

in which
$R^1$, $R^4$ and Hal have the abovementioned meaning.

DESCRIPTION

Lower alkyl radicals which may be mentioned are straight-chain and branched alkyl radicals with up to 8, preferably with up to 4, C atoms, for example the isomeric pentyl, hexyl, heptyl and octyl radicals, butyl, isobutyl, t.-butyl, propyl, isopropyl and especially ethyl and methyl.

Optionally substituted aryl radicals which may be mentioned are those with 6 to 14 C atoms in the aromatic system, preferably phenyl and naphthyl.

Substituents of the optionally substituted aryl radicals which may be mentioned are preferably halogen, lower alkyl, alkoxy and halogenoalkyl radicals, the nitro group and the hydroxyl group.

The abovementioned alkyl, alkoxy, and halogenoalkyl radicals have the same range of meaning, with regard to the carbon chain, as that indicated above for alkyl radicals.

Halogens which may be mentioned are fluorine, chlorine, bromine and iodine, bromine and especially chlorine being preferred.

Particularly preferred compounds of the formulae II and III are those in which
$R^1$ represents methyl, phenyl, 3-chlorophenyl, 3,4-dichlorophenyl, 3-nitrophenyl, 4-methylphenyl or 4-chloromethylphenyl and
Hal represents chlorine.

Further, it has been found that the new compounds of the formula II are obtained when compounds of the formula

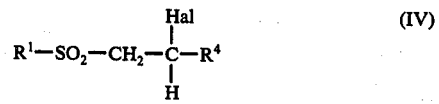

in which
$R^1$, $R^4$ and Hal have the abovementioned meaning are reacted, in the temperature range from 0 to 120° C, with at least the stoichiometrically required amount of a halogenating agent.

The reaction is preferably carried out in the temperature range between 10° and 110° C.

The starting compounds of the formula IV are known or can be prepared according to known processes. (Chemical Abstracts 61, 9437; 54, 15 319; 65, 12 134; 57, 8509; 57, P 4 604 f; 68; 12 663; 57, 8503; 62, 7 690–91). Starting compounds of formula IV are for example; β-halo-β-cyanoethyl-methyl-sulfone, β-halo-β-cyanoethyl-ethyl-sulfone, β-halo-β-cyanoethyl-isopropyl-sulfone, β-halo-β-cyanoethyl-propyl-sulfone, β-halo-β-cyanoethyl-tert.-butyl-sulfone, β-halo-β-cyanoethyl-isobutyl-sulfone, β-halo-β-cyanoethyl-butyl-sulfone, β-halo-β-cyanoethyl-pentyl-sulfone, β-halo-β-cyanoethyl-hexyl-sulfone, β-halo-β-cyanoethyl-heptyl-sulfone, β-halo-β-cyanoethyl-octyl-sulfone, β-halo-β-cyanoethyl-phenyl-sulfone, β-halo-β-cyanoethyl-4-chlorphenyl-sulfone, β-halo-β-cyanoethyl-4-methylphenyl-sulfone, β-halo-β-cyanoethyl-3-chlorophenyl-sulfone, β-halo-β-cyanoethyl-3-nitrophenyl-sulfone, β-halo-β-cyanoethyl-3,4-dinitrophenyl-sulfone, β-halo-β-cyanoethyl-4-chloromethylphenyl-sulfone, β-halo-β-cyanoethyl-4-hydroxyphenyl-sulfone, β-halo-β-cyanoethyl-4-methoxyphenyl-sulfone.

Halogenating agents which may be mentioned are the halogens (fluorine, chlorine, bromine and iodine,), preferably chlorine, sulphuryl halides, preferably sulphuryl chloride, and phosphorus halides, preferably phosphorus pentachloride.

At least the stoichiometrically required amount of halogenating agent must be employed; however, it can be advantageous to use an excess of halogenating agent, up to 3 times, especially up to twice, the minimum amount required.

The process according to the invention can also be carried out in the presence of solvents. For this purpose, solvents which are inert towards the halogenating agent used are preferably employed, for example ethers, such as dialkyl ethers, for example diethyl ether and diethylene glycol dimethyl ether, cyclic ethers, for example dioxane, lower aliphatic carboxylic acids, such as acetic acid, propionic acid and butyric acid, aliphatic and aromatic halogenohydrocarbons, such as ethylene chloride and chlorobenzene, but also acid chlorides such as thionyl chloride, benzenesulphonic acid chloride and toluenesulphonic acid chloride.

In general, the process according to the invention is carried out by bringing together the starting compound used, of the Formula IV, with the chosen halogenating agent, if appropriate in the presence of the chosen solvent, and allowing the compounds to react within the chosen temperature range until the conversion has ended. The end of the reaction can be determined in a simple manner by means of known analytical methods, for example by thin layer chromatography.

It can however also be advantageous to add the halogenating agent not all at once, but in several portions or continuously. In particular, the addition of the halogenating agent in portions or continuously will be advantageous if the halogenating agent is liquid (for example sulphuryl chloride) or gaseous (for example chlorine) or is employed in a liquid or gaseous form. When using a solvent it is not always necessary completely to dissolve the starting compound of the formula IV in the solvent; frequently, the reaction product is more readily soluble than the starting material, so that in order to save solvent it can be advantageous to suspend, and only partially dissolve, the starting compound of the formula IV in a smaller amount of the chosen solvent.

The choice of the halogenating agent depends advantageously on the starting compound of the formula IV which is employed; the most advantageous halogenating agent can be determined easily by a few preliminary experiments. In general, however, sulphuryl chloride is preferred as the halogenating agent.

The choice of the appropriate reaction temperature also depends on the choice of the halogenating agent; for example, higher temperatures are advantageous, or necessary, when using chlorine or phosphorus pentachloride as the halogenating agent, than when using sulphuryl chloride as the halogenating agent.

The working up of the reaction mixture and the isolation and, if appropriate, purification, can be carried out in the usual manner, for example by distilling off any excess of halogenating agent and solvent which may have been employed. Especially when using a gaseous halogenating agent, which can be passed into the solution of the starting compound in the usual manner, it is particularly simple to remove an excess.

Of course the reaction product can be purified further, afte isolation, in accordance with customary processes, for example by recrystallisation or distillation.

In general, the process according to the invention gives compounds of the formula I in which the halogen atom which has entered is in the α-position relative to the radical R$^4$, as shown by the NMR measurement. To separate off by-products it can however be advantageous and at times necessary to purify the resulting reaction product by chromatographic processes, preferably column chromatography, and separate off the by-products.

Further, it has been found that the new compounds of the formula III are obtained when the new compounds of the formula II are reacted with at least 1 mol of hydrogen halide acceptor in the presence of a solvent in the temperature range from 0° to 100° C.

The reaction is preferably carried out in the temperature range from 0° to 50° C. Hydrogen halide acceptors which can be used are the known hydrogen halide acceptors, such as aliphatic, aromatic and aliphatic-aromatic tertiary amines, for example triethylamine, pyridine and dimethylbenzylamine. Of course, in this context, cycloaliphatic and aliphatic-cycloaliphatic tertiary amines are includes amongst the aliphatic amines.

Further hydrogen halide acceptors which can be used are the hydroxides, acetates, carbonates, bicarbonates and alcoholates of the alkali metals and alkaline earth metals, for example sodium acetate, sodium methylate, sodium bicarbonate, calcium hydroxide and potassium carbonate.

The hydrogen halide acceptor is employed in an amount of at least 1 mol per mol of starting compound of the formula II. Of course, an excess of up to 3, preferably of up to 1.1, mols per mol of starting compound can also be used; however, the use of an excess in general produces no advantage; it can even lead to increased expense in isolating the reaction product, or to undesired side-reactions or secondary reactions.

The course of the reaction can be illustrated by the following equation for the example of 2,2-dichloro-2-cyanoethyl-phenylsulphone.

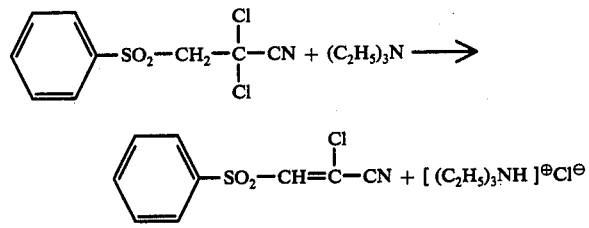

In general, the reaction according to the invention is carried out by dissolving the starting compound used, of the formula II, in an inert solvent and slowly metering in the chosen hydrogen halide acceptor in appropriate amount, within the chosen temperature range, and, if appropriate, allowing the reaction mixture to react further until the conversion has ended. The end of the reaction can easily be determined by customary analytical methods, for example by thin layer chromatography.

Suitably, the solvent used is chosen in the context of the hydrogen halide acceptor used. If tertiary amines are used as hydrogen halide acceptors, polar and non-polar solvents are in general equally suitable. On the other hand, when using the abovementioned alkali metal compounds and alkaline earth metal compounds it is advantageous to use polar solvents, such as lower aliphatic carboxylic acids, for example acetic acid and propionic acid.

Of course, it is not possible to use those of the abovementioned solvents which, though inert under the conditions of the halogenation reaction, are not inert under the conditions of elimination of hydrogen halide, for example thionyl chloride and benzenesulphonic acid chloride.

Furthermore it can be advantageous to use, for the elimination of hydrogen halide, solvents which are not inert under the conditions of the halogenation reaction, for example lower aliphatic alcohols, such as methanol and ethanol.

Furthermore it can be advantageous not to dissolve the starting compound of the formula II completely in the solvent but partially only to suspend it. Furthermore it can be advantageous not to carry out the reaction according to the invention in a liquid phase but at the interface of two liquid phases, that is to say to use, in addition to a water-immiscible solvent from amongst those mentioned above, a second phase consisting of water in which the hydrogen halide acceptor used is preferably soluble.

To work up the reaction mixture and isolate the reaction product, the salt of the hydrogen halide acid, formed as a by-product, and any excess hydrogen halide acceptor and/or aqueous phase are separated off in the usual manner, for example by filtering off salts which are insoluble in the reaction solution, by dissolving and/or by washing the organic reaction solution with water. Equally, the isolation of the reaction product can be carried out in the usual manner, for example by distilling off the solvent; if required, the reaction product can furthermore be purified in accordance with customary processes, for example by distillation or recrystallisation.

It has furthermore been found that the new compounds of the formula I exhibit an outstanding microbicidal activity, especially a bactericidal, fungicidal and algicidal action. In particular, the new compounds of the formulae II and III are active against fungi, such as Penicillium glaucum, Chaetomium globosum, Rhizopus nigricans and Aspergillus niger; bacteria, such as Bacterium coli, Bacterium pyocyaneum and Aerobacter aerogenes; slimes, such as slime-forming organisms which utilise caprolactam; algae, such as green algae, for example Stichococcus bacillaris Naegeli, Euglena gracilis Klebs and Chorella pyrenoidosa Chick, blue algae, for example Phormidium foredarum Gromont and Oscillatoria geminata Meneghini and silicaceous algae, for example Phaedodactylum tricornutum Bohlin.

Because of this action, the new microbicidal active compounds can find diverse uses in industrial protection of materials.

They are used with advantage for protecting aqueous systems such as solutions, emulsions, suspensions and dispersions, for example aqueous wash liquids and coolants and coolant-lubricants; they can be used preferentially for the protection of circulatory wash water and cooling water and of pulp feed channels of paper factories, in spinning baths in the manufacture of synthetic fibres, in electrophoresis baths in electrophoretic lacquering and in other aqueous solutions, suspensions and emulsions which are intended to remain ready-to-use for prolonged periods.

Equally, they can be used for protecting intermediate products, semi-finished goods and finished goods against undesired attack by microbes or microbial growth, for example in polymer dispersions, paper coating compositions, glues, wax emulsions, dyestuff suspensions, vegetable tanning liquors and oil-based or glue-based dyestuff formulations, and for preserving skins and leather.

Of course, the new compounds can also be used in the form of microbicidal agents; an example of the composition of a microbicidal agent is 25% of a compound according to the invention, 5 to 10% of emulsifier, for example aralkyl polyether, and 65 to 70% of hydrocarbon, for example xylene.

The amounts of the new compounds which are required to achieve a sufficient action against undesired microbial attack or microbial growth can in general be determined by a few experiments. They are in general between 0.0001 and 0.5 percent by weight. Preferably, between 0.01 and 0.03 percent by weight of the new compounds are employed when used to preserve goods packaged in containers, 0.002 to 0.2 percent by weight when used to protect coolant-lubricants, spinning preparations, wax emulsions, filler suspensions and spreading compositions, and 0.00001 to 0.01 percent by weight when used as an agent for combating algae and slimes for protecting wash liquors and coolants and paper pulp suspensions in paper manufacture.

The use of microbicidal active compounds and microbicidal agents in the fields mentioned is, to that extent, part of the state of the art and the new microbicidal compounds can be used in the customary manner by those skilled in the art.

Of course it is also possible to use the new microbicidal compounds in the usual manner as a mixture with microbicides known from the state of the art.

The new compounds contribute to an enrichment of the state of the art in that they serve to provide further microbicidal active compounds.

EXAMPLES

After completion of the reaction, the working up of the reaction mixture was carried out in the same manner in each of the Examples 1a and b), and 2 to 6, which follow: the reaction solution was concentrated in a rotary evaporator the residue was dissolved in 200 to 2,000 ml of methylene chloride, depending on the amount, and the solution was extracted by shaking with twice 50 to 1,000 ml of water. After drying the methylene chloride with sodium sulphate and distilling off the methylene chloride, the particular reaction product was in each case left as a residue described in the individual examples.

EXAMPLE 1

(a) 30 g (0.13 mol) of $\beta$-chloro-$\beta$-cyano-ethyl-phenyl-sulphone and 30 g (0.23 mol) of sulphuryl chloride are stirred for 15 hours at room temperature, whereby an orange-yellow solution is produced, with evolution of HCl and SO$_2$. After working up as described above, 33 g (96% of theory) of $\beta,\beta$-dichloro-$\beta$-cyano-ethyl-phenyl-sulphone are obtained as an oil which solidified on cooling, to give a colourless crystal mass. After one recrystallisation from ethanol, the compound melts at 73° to 74° C.

(b) A moderate stream of chlorine is passed for 5 hours into a melt of 30 g of $\beta$-chloro-$\beta$-cyano-ethyl-phenyl-sulphone, to which 0.3 g of iron-(III) chloride has been added, at a temperature of about 120° C. Thereafter the melt is allowed to cool, taken up in 200 ml of methylene chloride and extracted by shaking with twice 50 ml of water. After drying the methylene chloride solution with sodium sulphate and distilling off the methylene chloride, 15 g (45% of theory) of $\beta,\beta$-dichloro-$\beta$-cyano-ethyl-phenyl-sulphone are left.

(c) 11.5 g (0.05 mol) of $\beta$-chloro-$\beta$-cyano-ethyl-phenyl-sulphone and 20.8 g (0.1 mol) of phosphorus pentachloride in 100 ml of chlorobenzene are heated to about 110° C for 3 hours. After cooling, the reaction mixture is extracted by shaking with twice 50 ml of water. After drying the chlorobenzene solution over sodium sulphate and distilling off the solvent, 11 g (80% of theory) of $\beta,\beta$-dichloro-$\beta$-cyano-ethyl-phenyl-sulphone are left.

EXAMPLE 2

66 g (0.25 mol) of $\beta$-chloro-$\beta$-cyano-ethyl-3-chlorophenyl-sulphone and 60 g (0.46 mol) of sulphuryl chloride are stirred for 24 hours at 25° C. The reaction product is worked up as described and gives 73 g (98% of theory) of $\beta,\beta$-dichloro-$\beta$-cyano-ethyl-3-chlorophenyl-sulphone of melting point 93° C (after recrystallisation from ethanol).

EXAMPLE 3

47 g (0.28 mol) of β-chloro-β-cyano-ethyl-methyl-sulphone and 40 g (0.3 mol) of sulphuryl chloride are stirred for 36 hours at 20° to 25° C. The reaction product is worked up as described and gives 40.5 g (67% of theory) of β-β-dichloro-β-cyano-ethyl-methyl-sulphone. Light brown oil, density 1.48 (25° C), which solidifies on standing, melting point 70° C (after recrystallisation from ethanol).

EXAMPLE 4

217 g (0.95 mol) of β-chloro-β-cyano-ethyl-phenyl-sulphone and 870 g (6.4 mols) of sulphuryl chloride are stirred for 30 hours at 40° C. The excess sulphuryl chloride is distilled off in vacuo. The reaction product is worked up as described and gives 164 g (61% of theory) of α,α-dichloro-β-phenylsulphonyl-propionic acid amide of melting point 122° C (after recrystallisation from ethanol).

EXAMPLE 5

60 g (0.2 mol) of β-chloro-β-cyano-ethyl-3,4-dichlorophenyl-sulphone and 67 g (0.5 mol) of sulphuryl chloride was stirred for 24 hours at 45° C. The excess sulphuryl chloride is distilled off in vacuo. The reaction product is worked up as described and gives 46 g (65% of theory) of α,α-dichloro-β-3,4-dichlorophenylsulphonyl-propionic acid amide of melting point 120° C (after recrystallisation from ethanol).

EXAMPLE 6

205 g (1.24 mols) of β-chloro-β-cyano-ethyl-methyl-sulphone and 350 g (2.6 mols) of sulphuryl chloride are stirred for 24 hours at 35° to 40° C. The excess sulphuryl chloride is distilled off in vacuo. The reaction product is worked up as described and gives 150 g (53% of theory) of α,α-dichloro-β-methylsulphonyl-propionic acid amide of melting point 120° C (after recrystallisation from chloroform).

EXAMPLE 7

50 g (0.19 mol) of β,β-dichloro-β-cyano-ethyl-phenyl-sulphone are dissolved in 100 ml of 1 : 1 acetone/ethanol and 19 g (0.19 mol) of triethylamine are added slowly at 10° to 15° C. The mixture is then stirred for a further hour at room temperature, the triethylamine hydrochloride which has precipitated is filtered off, the solution is concentrated and the residue is recrystallised from ethanol: 29.5 g (69% of theory) of α-chloro-β-phenylsulphonylacrylonitrile of melting point 88° C; colourless crystals.

EXAMPLE 8

33.5 g (0.11 mol) of β,β-dichloro-β-cyano-ethyl3-chlorophenyl-sulphone are dissolved in 280 ml of a 1 : 1 mixture of diethyl ether and acetone and 11.2 g (0.11 mol) of triethylamine are added slowly at 10° to 13° C. The mixture is then worked up as described in Example 7. After recrystallisation from ethanol, 10 g (35% of theory) of α-chloro-β-3-chlorophenyl-sulphonyl-acrylonitrile are obtained: colourless crystals of melting point 150° C.

EXAMPLE 9

67 g (0.5 mol) of sulphuryl chloride are added dropwise to a mixture of 40 g (0.16 mol) of β-chloro-β-cyano-ethyl-4-methylphenyl-sulphone, 60 g (0.32 mol) of toluenesulphonic acid chloride and 26 g of chlorobenzene at 30° C, whilst stirring. The mixture is stirred for a further 24 hours, volatile constituents are then distilled off at 60° C in a waterpump vacuum and the hot residue is stirred with 200 ml of ligroin. The crystal mixture produced after standing for several hours is recrystallised from 150 ml of butanol. 35 g (77% of theory) of β,β-dichloro-β-cyano-ethyl-4-methylphenyl-sulphone of melting point 71° to 72° C are thus obtained.

EXAMPLE 10

6.1 g (0.045 mol) of dimethylbenzylamine are added dropwise, whilst stirring, to a solution of 12.5 g (0.045 mol) of β,β-dichloro-β-cyano-ethyl-4-methylphenyl-sulphone in 125 ml of ethanol at 15° C. After stirring for a further 2 hours at room temperature, the reaction mixture is poured onto 1 l of water and the crystals formed are filtered off and dried. 10 g (91% of theory) of α-chloro-β-(4-methylphenyl-sulphonyl)-acrylonitrile of melting point 78° are obtained.

EXAMPLE 11

50 g (0.18 mol) of β-chloro-β-cyano-ethyl-4-nitrophenyl-sulphone and 27 g (0.2 mol) of sulphuryl chloride are stirred for 24 hours at 25° C. Volatile constituents are then distilled off in a waterpump vacuum at 60° C and thereafter volatile constituents are distilled off in a waterpump vacuum at 60° C and the oily residue is charged onto a column of dry silica gel. The material is then chromatographed and eluted with benzene, the individual fractions being collected separately. After distilling off (the solvent), the middle fraction gives 7 g (13% of theory) of β,β-dichloro-β-cyano-ethyl-4-nitrophenyl-sulphone in the form of a yellowish oil which crystallises on standing. After recrystallisation from ethanol, the compound melts at 86° C.

EXAMPLE 12

7 g (0.03 mol) of β-chloro-β-cyano-ethyl-4-chloromethylphenyl-sulphone are stirred with 4.0 g (0.03 mol) of sulphuryl chloride for 24 hours at room temperature; volatile constituents are then distilled off at 60° C in a waterpump vacuum and the reaction product is charged onto a dry silica gel column and chromatographed and eluted with benzene. The main fraction, after evaporation of the benzene, gives 6.3 g (72% of theory) of β,β-dichloro-β-cyano-ethyl-4-chloromethylphenyl-sulphone of melting point 84° C (after recrystallisation from ethanol).

EXAMPLE A

The compounds of Table I, in concentrations of 0.1 to 100 mg/l, were introduced into Allen's nutrient solution, which contained 1% of caprolactam as a source of carbon and additional source of nitrogen, as a solution in a little acetone. Shortly beforehand, the nutrient solutions were infected with slime organisms (about $10^6$ germs/ml) which were isolated from spinning water circulation systems used in the manufacture of polyamide. Nutrient solutions which contained the minimum microbistatic concentration (MMC) or higher concentrations of active compound were still completely clear even after three weeks' culture at room temperature, that is to say the marked multiplication of microbes, and slime formation, noticeable after 3 to 4 days in nutrient solutions free from active compound did not occur. The MMC values listed in Table I show the excellent antimicrobial activity, especially the activity of the compound according to the invention against slime organisms.

colour as a result of intensive growth of algae. Even small additions of substances according to the invention caused the algae to die and the nutrient solution again to lose its colour.

Table I

Test organisms: slime-forming organisms which utilise caprolactam

| Compound | MMC (mg/l) |
|---|---|
| β,β-Dichloro-β-cyano-ethyl-phenyl-sulphone | 0.3 |
| β,β-Dichloro-β-cyano-ethyl-3-chlorophenyl-sulphone | 0.3 |
| β,β-Dichloro-β-cyano-ethyl-4-methylphenyl-sulphone | 0.2 |
| β,β-Dichloro-β-cyano-ethyl-methyl-sulphone | 0.2 |
| α,α-Dichloro-β-phenylsulphonyl-propionic acid amide | 0.5 |
| α,α-Dichloro-β-3,4-dichlorophenylsulphonyl-propionic acid amide | 0.5 |
| α,α-Dichloro-β-methylsulphonyl-propionic acid amide | 0.2 |
| α-Chloro-β-phenylsulphonyl-acrylonitrile | 0.2 |
| α-Chloro-β-3-chlorophenylsulphonyl-acrylonitrile | 0.2 |

EXAMPLE B (Action against moulds and yeasts)

Concentrations of 2 mg/l to 5,000 mg/l of the compounds of the Table II were worked into an agar which was prepared from beer wort and peptone. When the agar had solidified, it was contaminated with pure cultures of *Penicillium glaucum, Chaetomium globosum* and *Aspergillus niger.* After two weeks' storage at 28° C and 60 to 70% relative atmospheric humidity the results were evaluated. The MMC is the lowest concentration of active compound at which no growth of the species of microbe used took place; it is shown in Table II below.

Table IV

Concentrations, in mg/l, of compounds according to the invention which cause a mixed culture of algae to die

| Compound | Concentration (mg/l) |
|---|---|
| β,β-Dichloro-β-cyano-ethyl-phenyl-sulphone | 50 |
| α,α-Dichloro-β-methylsulphonyl-propionic acid amide | 30 |
| α-Chloro-β-phenylsulphonyl-acrylonitrile | 50 |

EXAMPLE E

Table II

| Compound | Penicillium glaucum MMC (mg/l) | Chaetomium globosum MMC (mg/l) | Aspergillus niger MMC (mg/l) |
|---|---|---|---|
| β,β-Dichloro-β-cyano-ethyl-phenyl-sulphone | 75 | 75 | 50 |
| β,β-Dichloro-β-cyano-ethyl-3-chlorophenyl-sulphone | 150 | 100 | 50 |
| α,α-Dichloro-β-methyl-sulphonyl-propionic acid amide | 200 | 350 | 500 |
| α-Chloro-β-phenylsulphonyl-acrylonitrile | 35 | 50 | 50 |
| α-Chloro-β-3-chlorophenyl-sulphonyl-acrylonitrile | 75 | 50 | 50 |

EXAMPLE C (Action against bacteria)

A bouillon agar was provided with substances of Table III in the same manner as in Example B; it was then contaminated with *Bacterium coli* and *Bacterium pyocyaneum,* incubated and evaluated after 2 weeks:

Table III

| Compound | Bacterium coli MMC (mg/l) | Bacterium pyocyaneum MMC (mg/l) |
|---|---|---|
| β,β-Dichloro-β-cyano-ethyl-phenyl-sulphone | 200 | 200 |
| β,β-Dichloro-β-cyano-ethyl-3-chlorophenyl-sulphone | 200 | 500 |
| α,α-Dichloro-β-methylsulphonyl-propionic acid amide | 100 | 75 |
| α-Chloro-β-phenylsulphonyl-acrylonitrile | 200 | 500 |
| α-Chloro-β-3-chlorophenylsulphonyl-acrylonitrile | 1,500 | 2,000 |

EXAMPLE D

A mixed culture of green algae, blue algae, brown algae and silicaceous algae (*Stichococcus bacillaris Naegeli, Euglena gracilis Klebs, Chlorella pyrenoidose Chick, Phormidium foredarum Gromont, Oscillatoria geminata Meneghini* and *Phaedodactylum tricornutum Bohlin*) was introduced, in the laboratory, into Allen's nutrient solution (M. B. Allen, Arch. Mikrobiol. 17, 34 to 53, 1952), whilst bubbling air through the solution. After two weeks, the nutrient solution was a deep green-blue in The addition of as little as 8 ppm of β,β-dichloro-β-cyano-ethyl-phenyl-sulphone or α-chloro-β-phenylsulphonyl-acrylonitrile to a back water sample, from a paper factory, containing $1.5 \times 10^8$ germs (predominantly slime-forming organisms) per ml cause complete destruction of the germs within 24 hours.

EXAMPLE F

The superior activity of the new compounds according to the invention, as compared to the previously known starting compounds, is shown by the following examples:

(a) The addition of 40 ppm of β,β-dichloro-β-cyano-ethyl-phenyl-sulphone or α-chloro-β-phenylsulphonyl-acrylonitrile to a back water sample, from a paper factory, which contained $9.3 \times 10^7$ germs (predominantly slime-forming organisms) per ml, caused complete destruction of the germs within 2 to 5 hours, whilst even 70 ppm of β-chloro-β-cyano-ethyl-phenyl-sulphone only gave a reduction to $2.5 \times 10^7$ germs per ml.

(b) A water sample from a cooling circuit heavily infected with microbes contained $1.4 \times 10^6$ germs per ml. Additions of 0.8 ppm of β,β-dichloro-β-cyano-ethyl-phenyl-sulphone or α-chloro-β-phenylsulphonyl-acrylonitrile gave a reduction to $6.8 \times 10^4$ (95%) germs per ml after 18 hours at 30° C and additions of 7 ppm achieved complete destruction. 7 ppm of β-chloro-β-cyano-ethyl-phenyl-sulphone, on the other hand, merely achieved a reduction to $1.4 \times 10^5$ germs per ml.

What is claimed is:

1. Compound having the formula $$R^1-SO_2-CH=\underset{\underset{\text{Hal}}{|}}{C}-R^4$$

wherein
- $R^1$ is alkyl having up to 8 carbon atoms which can optionally be substituted by a halogen or aryl having 6 to 14 carbon atoms in the aromatic ring which can optionally be substituted with a halogen, lower alkyl, alkoxy, halogenoalkyl, nitro or hydroxyl group,
- $R^4$ is nitrile or carboxylic acid amide and Hal is halogen.

2. Compounds of claim 1 wherein $R^1$ is methyl, phenyl, 3-chlorophenyl, 3,4-dichlorophenyl, 3-nitrophenyl or 4-chloro-methylphenyl and Hal is chlorine.

3. Compound of claim 1 wherein $R^4$ is a nitrile group.

4. Compound of claim 1 wherein $R^4$ is a carboxylic acid amide group.

5. Process for preparing compounds of claim 1 which comprises reacting compounds having the formula $$R^1-SO_2-\underset{\underset{H}{|}}{CH}-\underset{\underset{\text{Hal}}{|}}{\overset{\overset{\text{Hal}}{|}}{C}}-R^4$$

wherein
- $R^1$ is optionally halogen-substituted lower alkyl or optionally substituted aryl,
- $R^4$ is nitrile or carboxylic acid amide and
- Hal is halogen, with at least 1 mol of a hydrogen halide acceptor in the presence of a solvent at temperatures in the range from 0° to 100° C.

6. An antimicrobial composition comprising an antimicrobially effective amount of a compound having the formula $$R^1-SO_2-CH=\underset{\underset{\text{Hal}}{|}}{C}-R^4$$

wherein
- $R^1$ is optionally halogen-substituted lower alkyl or optionally substituted aryl,
- $R^4$ is nitrile or carboxylic acid amide and
- Hal is halogen;

in a solution, suspension, emulsion or dispersion.

* * * * *